United States Patent [19]
Sasaki et al.

[11] Patent Number: 4,701,209
[45] Date of Patent: Oct. 20, 1987

[54] ALUMINUM PHOSPHINATE-AMINE ADDUCTS, AND THEIR PRODUCTION AND USE

[75] Inventors: Mitsuru Sasaki; Yukio Oguri, both of Toyonaka, Japan

[73] Assignee: Sumitomo Chemical Company, Limited, Osaka, Japan

[21] Appl. No.: 865,967

[22] Filed: May 22, 1986

[30] Foreign Application Priority Data

Jun. 5, 1985 [JP] Japan ............................ 60-121946

[51] Int. Cl.$^4$ .................. C07F 5/06; A01N 55/02
[52] U.S. Cl. ............................... 71/97; 556/174
[58] Field of Search ......................... 556/174; 71/97

[56] References Cited

U.S. PATENT DOCUMENTS

| 2,329,707 | 9/1943 | Farrington et al. | 556/174 X |
| 2,758,971 | 8/1956 | Mikeska | 556/174 X |
| 3,305,330 | 2/1967 | McCoy et al. | 556/174 X |
| 3,477,953 | 11/1969 | Carlson | 556/174 X |
| 4,139,616 | 2/1979 | Ducret et al. | 556/174 X |
| 4,143,059 | 3/1979 | Abblard et al. | 556/174 |
| 4,473,561 | 9/1984 | Ishiguri et al. | 514/114 |

OTHER PUBLICATIONS

Chemical Abstracts, 67, 4673c, (1967).

Primary Examiner—Helen M. S. Sneed
Attorney, Agent, or Firm—Birch, Stewart, Kolasch & Birch

[57] ABSTRACT

Aluminum phosphinate-amine adducts of the formula:

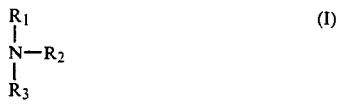

wherein $R_1$, $R_2$ and $R_3$ are each a hydrogen atom, a lower alkyl group, a lower alkoxy(lower)alkyl group, a lower alkylthio(lower)alkyl group or a cyclo(lower)alkyl group to aluminum 1-hydroxyethylphosphinate-amine, which are useful for prevention and treatment of plant diseases caused by phytopathogenic fungi.

9 Claims, No Drawings

ALUMINUM PHOSPHINATE-AMINE ADDUCTS, AND THEIR PRODUCTION AND USE

The present invention relates to aluminum phosphinate-amine adducts, their production and use. More particularly, it relates to the adducts of amines of the formula:

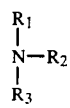

wherein $R_1$, $R_2$ and $R_3$ are each a hydrogen atom, a lower alkyl group, a lower alkoxy(lower)alkyl group, a lower alkylthio(lower)alkyl group or a cyclo(lower)alkyl group to aluminum 1-hydroxyethylphosphinate, their production and use.

In the present specification, the term "lower" is intended to mean a group having not more than about 8 carbon atoms, preferably not more than about 6 carbon atoms.

The adducts of the invention are usually obtained in crystals which do not have specific melting points, and in which the equivalent ratio of the amine and the aluminum 1-hydroxyethylphosphinate is from about 0.5 to 2.0:1. Their typical product is the 1:1 adduct of the formula:

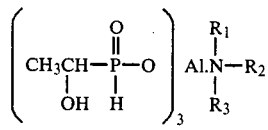

wherein $R_1$, $R_2$ and $R_3$ are each as defined above.

It has now been found that said adducts not only show a preventive effect but also a curative effect against plant diseases caused by phytopathogenic fungi. Examples of the phytopathogenic fungi against which the adducts of the invention can exert their fungicidal activity are *Diaporthe citri*, *Elsinoe fawcetti*, *Penicillium digitatum* and *Penicillium italicum* on citrus fruit; *Sclerotinia mali*, *Valsa mali*, *Podosphaera leucotricha*, *Alternaria mali* and *Venturia inaequalis* on apple; *Venturia nashicola*, *Alternaria kikuchiana* and Glymnosporangium haracanum on pear; *Sclerotinia cinerea*, *Cladosporium carpophilum* and *Phomopsis* sp. on peach; *Glomerella cingulata*, *Uncinula necator* and *Phakopsora ampelopsidis* on grape; *Gloeosporium kaki*, *Cercospora kaki* and *Mycosphaerella nawae* on kaki; *Colletotrichum lagenarium*, *Sphaerotheca fuliginea* and *Mycosphaerella melonis* on melon; *Alternaria solani* and *Cladosporium fulvum* on tomato; *Phomopsis vexans* and *Erysiphe cichoracerum* on eggplant; *Alternaria japonica* and *Cercosporella brassicae* on Cruciferde vegetables, *Puccinia allii* on onion; *Cercospora kikuchii*, *Elsinoe glycines* and *Diaporthe phaseolorum* var. *sajae* on soybean; *Colletotrichum lindemuthianum* on kidney bean; *Mycosphaerella personatum* and *Cercospora arachidicola* on peanut; *Erysiphe pisi* on peas; *Alternaria solani* on potato; *Sphaerotheca humuli* on strawberry; *Exobasidium reticulatum* and *Elsinoe leucospila* on tea tree; *Alternaria longipes*, *Erysiphe cichoracearum* and *Colletotrichum tabacum* on tobacco; *Cercospora beticola* on sugarbeet; *Diplocarpon rosae* and *Sphaerotheca pannosa*) on rose; *Septoria chrysanthemi-indici* and *Puccinia horiana* on chrysanthemate; *Botrytis cinerea* and *Sclerotinia sclerotiorum* on various crop plants; *Peronospora brassicae* on vegetables including radish; *Peronospora spinaciae* on spinach; *Peronospora tabacina* on tobacco; *Pseudoperonospora cubensis* on cubumer; *Plasmopara viticola* on grape; *Plasmopara nivea* on dropwort plants; *Phytophthora cactorum* on apple, strawberry or medicinal carrot; *Phytophthora capsici* on tomato or cucumber; *Phytophthora cinnamomi* on pineapple; *Phytophthora infestans* on potato, tomato or eggplant; *Phytophthora nicotianae* var. *nicothianae* on tobacco, horsebean or onion; *Pythium aphanidermatum* on cucumber; *Phythium* sp. on spinach; *Pythium* sp. and *Peudocercosporella herpotrichoides* on wheat; *Pythium debaryanum* on tobacco; *Pythium aphanidermatum*, *P. debaryanum*, *P. myriotylum* and *P. ultimum* on sobean, etc.

Accordingly, they can be used as fungicides applicable to plowed fields, orchards, tea-garden, mulberry garden, meadow, lawn and so on.

The adducts of the invention are each obtainable by reacting aluminum 1-hydroxyethylphosphinate of the formula:

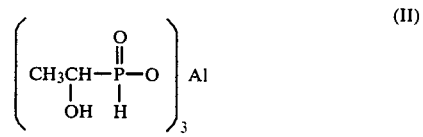

with the amine (I) in an amount of about 0.5 to 2.0 equivalent to the former in an aqueous medium, ordinarily at a temperature of about 0° to 60° C. for a period of about 1 to 12 hours, optionally followed by a conventional post-treatment such as filtration, decantation, concentration and recrystallization.

Preferred amines are those of the formula (I) wherein $R_1$, $R_2$ and $R_3$ are each a hydrogen atom, a $C_1$-$C_6$ alkyl group, a $C_1$-$C_6$ alkoxy($C_1$-$C_6$)alkyl group, a $C_1$-$C_6$ alkylthio($C_1$-$C_6$)alkyl group or a cyclo($C_3$-$C_6$)alkyl group. More preferred are those wherein $R_1$, $R_2$ and $R_3$ are each a hydrogen atom, a $C_1$-$C_6$ alkyl group or a cyclo($C_3$-$C_6$)alkyl group. The most preferred amines are those wherein $R_1$, $R_2$ and $R_3$ are each a hydrogen atom, a $C_3$-$C_6$ alkyl group or a cyclo($C_5$-$C_6$)alkyl group. Even more preferred are those wherein $R_1$ and $R_2$ are each a hydrogen atom and $R_3$ is a t-butyl group.

The starting aluminum 1-hydroxyethylphosphinate (II) may be prepared, for instance, by the known method as described in U.S. Pat. No. 4,473,561. Still, an aqueous solution of aluminum 1-hydroxyethylphosphinate (II) prepared by an alkali metal salt of 1-hydroxyethylphosphinic acid with an aluminum salt such as aluminium nitrate or aluminium sulfate in an aqueous medium may be as such used for the reaction with the amine (I) so as to obtain the adduct of the invention.

Practical and presently preferred embodiments for preparation of the adducts are illustratively shown in the following examples.

EXAMPLE 1

1-Hydroxyethylphosphinic acid (5.5 g; 0.05 mol) was dissolved in water (50 ml), and the resultant solution was neutralized with a 20% aqueous sodium hydroxide solution, followed by addition of Al(NO$_3$)$_3$.9H$_2$O (6.25 g; 0.017 mol) at 10 to 15° C. The reaction mixture was stirred at 20 to 25° C. for 3 hours, and t-butylamine (3.7 g; 0.05 mol) was added thereto at the same temperature. After stirring for 8 hours, the precipitated crystals were collected by filtration. Yield, 7.8 g (54.8%).

¹H-NMR (determined in deuterium oxide acidified with hydrochloric acid using TMS as an external standard): δ (ppm): 1.70 (9H, q, J=8 Hz and 16 Hz, CH₃CH—), 1.75 (9H, (CH₃)₃C—), 4.20–4.65 (3H, m,

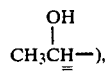

7.15 (3H, broad d, J=546 Hz, P-H).

EXAMPLE 2

Aluminium 1-hydroxyethylphosphinate (3.5 g; 0.01 mol) was dissolved in water (30 ml), followed by addition of 2-methoxyethylamine (1.2 g; 0.015 mol) at 0° to 5° C. The reation mixture was kept at 25° to 30° C. for 30 minutes and the precipitated crystals were collected by filtration. Yield, 1.8 g (42.3%).

¹H-NMR (determined in deuterium oxide acidified with hydrochloric acid using TMS as an external standard): δ (ppm): 1.75 (9H, q, J=8 Hz and 16 Hz,

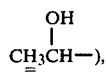

3.20–3.60 (4H, m, OCH₂CH₂N), 3.80 (3H, CH₃O), 4.20–4.70 (3H, m,

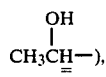

7.20 (3H, broad d, J=540 Hz, P-H).

EXAMPLE 3

Aluminum 1-hydroxyethylphosphinate (3.5 g; 0.01 mol) was dissoved in water (30 ml), followed by addition of cyclopentylamine (1.30 g; 0.015 mol) at 10° to 15° C. The reaction mixture was kept at the same temperature for 2 hours and at 25° to 30° C. for 12 hours, and the precipitated crystals were collected by filtration. Yield, 2.1 g (54.0 %).

¹H-NMR (determined in deuterium oxide acidified with hydrochloric acid using TMS as an external standard): δ (ppm): 1.70 (9H, q, J=8 Hz and 16 Hz,

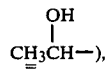

4.20–4.65 (3H, m,

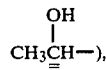

7.15 (3H, broad d, J=540 Hz, P-H), 1.50–2.00 (8H, broad

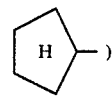

In the same manner as above, there were obtained the adducts of the invention, of which typical examples are shown in Table 1.

TABLE 1

$$\left( \begin{array}{c} \text{O} \\ \| \\ \text{CH}_3\text{CH}-\text{P}-\text{O} \\ | \quad | \\ \text{OH} \quad \text{H} \end{array} \right)_3 \text{Al.N} \begin{array}{c} R_1 \\ | \\ -R_2 \\ | \\ R_3 \end{array}$$

| Compound No. | R₁ | R₂ | R₃ | Physical property |
|---|---|---|---|---|
| 1 | H | H | t-C₄H₉ | ~220° C. (dec.) |
| 2 | H | H | i-C₃H₇ | ~210° C. (dec.) |
| 3 | H | H | s-C₄H₉ | ~220° C. (dec.) |
| 4 | H | H | CH₃OCH₂CH₂— | ~200° C. (dec.) |
| 5 | H | H | CH₃SCH₂CH₂— | Powder |
| 6 | H | H | n-C₅H₁₁ | ~210° C. (dec.) |
| 7 | H | C₂H₅ | C₂H₅ | Powder |
| 8 | H | H | n-C₃H₇ | Powder |
| 9 | H | i-C₃H₇ | i-C₃H₇ | Powder |
| 10 | H | H |  | ~190° C. (dec.) |

For practical application of the adducts of the invention as fungicides, they may be used alone without incorporation of other ingredients therein. For easier application, however, they are normally incorporated with preparation aids such as solid or liquid carriers or diluents and surfactants to formulate preparations such as wettable powders, suspensions, granules, dusts, etc. In these preparations, the content of the adducts as the active ingredient may be usually from about 0.1 to 99.9% by weight, preferably from about 1 to 99% by weight. As the solid carriers or diluents, there may be exemplified kaolin clay, attapulgite clay, bentonite, terra abla, pyrophyllite, talc, diatomaceous earth, calcite, corn stem powder, walnutshell powder, urea, ammonium sulfate, fine powder or granule of synthetic hydrated silica, etc. As the liquid carriers or diluents, there may be employed aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc. In addition to the solid or liquid carriers or diluents as exemplified above, there may be used ionic or non-ionic surfactants for emulsification, dispersion or streading when desired. Examples of the ionic surfactants are alkyl sulfate, alkylaryl sulfonate, dialkylsulfosuccinate, polyoxyethylene alkylaryl phosphonate, condensate of naphthalenesulfonate and formalin. Examples of the non-ionic surfactants are polyoxyethylene alkyl ether, polyoxyethylene polyoxypropylene block copolymer, sorbitan fatty acid ester, polyoxyethylene sorbitan fatty acid ester, etc. There may be also used auxiliary agents such as ligninsulfonate, alginate, polyvinyl alcohol, gum arabic, CMC (carboxymethylcellulose), PAP (isopropyl acid phosphate), etc.

Some typical examples of the fungicidal composition of this invention are shown below. In those examples, part(s) and % are by weight unless otherwise indicated.

FORMULATION EXAMPLE 1

Each of Compound Nos. 1 to 10 (50 parts), calcium ligninsulfonate (3 parts), sodium laurylsulfonate (2 parts) and synthetic hydrated silica (45 parts) are well mixed while being powdered to obtain a wettable powder.

FORMULATION EXAMPLE 2

Each of Compounds No. 1 to 10 (2 parts), synthetic hydrated silica (1 part), calcium ligninsulfonate (2 parts), bentonite (30 parts) and kaolin clay (65 parts) are thoroughly pulverized and mixed well with water. The mixture is granulated, followed by drying to obtain granules.

FORMULATION EXAMPLE 3

Each of Compounds No. 1 to 10 (25 parts), polyoxyethylene sorbitan monooleate (3 parts), CMC (3 parts) and water (69 parts) are mixed and pulverized. Pulverization under wet conditions is continued until the particle size of the active ingredient becomes less than 5 microns to obtain a suspension.

FORMULATION EXAMPLE 4

Each of Compound Nos. 1 to 10 (2 parts), kaolin clay (88 parts) and talc (10 parts) are thoroughly pulverized and mixed well with water to obtain a dust.

The composition may be applied as such or sprayed after dilution with water over the top of the plants by foliar treatment. Alternatively, the composition may be spread, mixed or incorporated into the soil. In order to improve the fungicidal activity, the composition may be used with other plant disease controlling agents. Further, they can be applied in combination with insecticides, acaricides, nematocides, herbicides, plant growth regulators, fertilizers, soil improvers, etc.

A suitable amount of the fungicidal composition of the invention to be applied is generally from about 0.5 to 200 grams, preferably from about 1 to 100 grams, in terms of the active ingredient per are. When the composition is in the form of wettable powder, emulsifiable concentrate or aqueous solution, it is normally diluted with water and then applied. The concentration of the active ingredient on the application may be within the range of about 0.005 to 2% by weight, preferably about 0.01 to 1% by weight. In case of the composition being in the form of dust or granule, it is ordinarily applied as such. Since, however, the amount and concentration largely depend upon composition forms, application times, application methods, application sites, diseases and crops, they may be increased or decreased appropriately.

The following examples show some typical test results supporting the excellent fungicidal activity of the adducts. In these examples, the compound numbers correspond to those in Table 1. The compounds used for comparison are as follows:

| Compound No. | Structure | Remarks |
| --- | --- | --- |
| A | $(C_2H_5-O-\overset{O}{\underset{H}{P}}-O)_3 Al$ | Commercially available fungicide "alliette" |
| B | Cl,Cl,Cl,Cl-substituted benzene with 2 CN groups | Commercially available fungicide "chlorothalonil" |

TEST EXAMPLE 1

Seeds of potato (species: "Danshaku") were sowed in sandy soil filled in plastic pots and cultivated in a greenhouse for 40 days to obtain seedlings. A spore suspension of *Phytophthora infestans* was sprayed onto the seedlings, which were placed at 20° C. under a humid condition for 1 day. Then, an aqueous dilution of the test compound in the form of wettable powder according to Formulation Example 1 was sprayed over the foliage of the test plant so as to thoroughly moisten the leaf surface. The test plant was further grown for 7 days under light, and the preventive value was critisized by vidual observation of the fungus plexus or diseased spot on leaf or stem of the test plant. The determination was made on the following criteria:

| Index | State of infection |
|---|---|
| 5 | No infectious spot on leaf or stem |
| 4 | Infectious spots of about 10% |
| 3 | Infectious spots of about 30% |
| 2 | Infectious spots of about 50% |
| 1 | Infectious spots of about 70% |
| 0 | Infectious spots of more than 70%; infectious spots being substantially equal to non-treated plants. |

The results are shown in Table 2.

TABLE 2

| Compound No. | Concentration of active ingredient (ppm) | Preventive value |
|---|---|---|
| 1 | 500 | 4 |
| 2 | 500 | 4 |
| 3 | 500 | 4 |
| 4 | 500 | 4 |
| 5 | 500 | 4 |
| 6 | 500 | 4 |
| 7 | 500 | 4 |
| 8 | 500 | 4 |
| 9 | 500 | 4 |
| 10 | 500 | 4 |
| A | 500 | 2 |
| B | 500 | 0 |

TEST EXAMPLE 2

Seeds of tomato (species: "Ponterosa") were sowed in sandy soil filled in plastic pots and cultivated in a greenhouse for 50 days until germination of 6-7 foliage leaf. An aqueous dilution of the test compound in the form of a wettable powder according to Formulation Example 1 was sprayed over the foliage of the test plant so as to thoroughly moisten the leaf surface. After the spraying, the test plants were cultivated in the greenhouse for 7 days and a spore suspension of *Phytophthora infestans* was sprayed thereover. After placing the plants at 20° C. for 1 day under a humid condition, they were further cultivated for 5 days under light. The preventive value was criticized in the same manner as in Test Example 1. The results are shown in Table 3.

TABLE 3

| Compound No. | Concentration of active ingredient (ppm) | Preventive value |
|---|---|---|
| 1 | 500 | 4 |
| 2 | 500 | 4 |
| 3 | 500 | 4 |
| 4 | 500 | 4 |
| 5 | 500 | 4 |
| 6 | 500 | 4 |
| 7 | 500 | 4 |
| 8 | 500 | 4 |
| 9 | 500 | 4 |
| 10 | 500 | 4 |
| A | 500 | 2 |
| B | 500 | 4 |

TEST EXAMPLE 3

Seeds of cucumber (species: "Sagamihanjiro") were sowed in sandy soil filled in plastic pots and cultivated in a greenhouse for 14 days until germination of cotyledon. A spore suspension of *Pseudoperonospora cubensis* was sprayed, and the test plants were placed at 20° C. for 1 day under a humid condition. An aqueous dilution of the test compound in the form of a suspension according the Formulation Example 3 was sprayed over the foliage of the test plant so as to thoroughly moisten the leaf surface. After the spraying, the test plants were cultivated in the greenhouse for 5 days under light. The preventive value was critisized in the same manner as in Test Example 1. The results are shown in Table 4.

TABLE 4

| Compound No. | Concentration of active ingredient (ppm) | Preventive value |
|---|---|---|
| 1 | 500 | 5 |
| 2 | 500 | 5 |
| 3 | 500 | 5 |
| 4 | 500 | 5 |
| 5 | 500 | 5 |
| 6 | 500 | 5 |
| 7 | 500 | 5 |
| 8 | 500 | 5 |
| 9 | 500 | 5 |
| 10 | 500 | 5 |
| A | 500 | 3 |
| B | 500 | 0 |

TEST EXAMPLE 4

Seeds of wheat (species: "Norin No. 73") were sowed in sandy soil filled in plastic pots and cultivated in a greenhouse for 10 days until germination of seedings. An aqueous dilution of the test compound in the form of wettable powder according to Formulation Example 1 was sprayed over the foliage of the test plant so as to thoroughly moisten the leaf surface. After the spraying, the test plants were air-dried and a spore suspension of *Pseudocercosporella herpotrichoides* was sprayed thereover. After placing the plants at 15° C. for 5 days under a humid condition, they were further grown for 5 days under light. The preventive value was criticized in the same manner as in Test Example 1. The results are shown in Table 5.

TABLE 5

| Compound No. | Concentration of active ingredient (ppm) | Preventive value |
|---|---|---|
| 1 | 500 | 4 |
| 2 | 500 | 4 |
| 3 | 500 | 4 |
| 4 | 500 | 4 |
| 5 | 500 | 4 |
| 6 | 500 | 4 |
| 7 | 500 | 4 |
| 8 | 500 | 4 |
| A | 500 | 0 |
| B | 500 | 1 |

TEST EXAMPLE 5

Seeds of tomato (species: "Ponterosa") were sowed in sandy soil filled in plastic pots and cultivated in a greenhouse for 30 days until germination of 3 to 4 foliage leaf. An aqueous dilution of the test compound in the form of a suspension according to Formulation Example 1 was sprayed over the foliage of the test plant so as to thoroughly moisten the leaf surface. After the spraying, a spore suspension of *Alternaria solani* was sprayed thereover. After placing the plants at 23° C. for 6 days under a humid condition, and the preventive value was criticized in the same manner as in Test Example 1. The results are shown in Table 6.

TABLE 6

| Compound No. | Concentration of active ingredient (ppm) | Preventive value |
|---|---|---|
| 1 | 500 | 5 |
| 2 | 500 | 5 |
| 3 | 500 | 4 |
| 4 | 500 | 5 |
| 7 | 500 | 4 |
| 10 | 500 | 3 |
| A | 500 | 0 |
| B | 500 | 4 |

TEST EXAMPLE 6

Seeds of cucumber (species: "Sagamihanjiro") were sowed in sandy soil filled in plastic pots and cultivated in a greenhouse for 14 days until germination of cotyledon. An aqueous dilution of the test compound in the form of a wettable powder according to Formulation Example 1 was sprayed over the foliage of the test plant so as to thoroughly moisten the leaf surface. After the spraying, a spore suspension of *Colletotrichum lagenarium* was sprayed thereover. After placing at 23° C. for 1 day under a humid condition, the test plants were further cultivated for 4 days under light. The preventive value was criticized in the same manner as in Test Example 1. The results are shown in Table 7.

TABLE 7

| Compound No. | Concentration of active ingredient (ppm) | Preventive value |
|---|---|---|
| 2 | 500 | 4 |
| 3 | 500 | 4 |
| 6 | 500 | 4 |
| 8 | 500 | 4 |
| 9 | 500 | 4 |
| 10 | 500 | 4 |
| A | 500 | 0 |

TEST EXAMPLE 7

Seeds of grape were sowed in sandy soil filled in plastic pots and cultivated in a greenhouse for 50 days until germination of 6 yo 7 foliage leaf. A spore suspension of *Plasmopara viticola* was sprayed onto the foliage and the test plants were placed at 20° C. for 1 day under a humid condition. An aqueous dilution of the test compound in the form of a wettable powder according to Formulation Example 1 was sprayed over the foliage of the test plant so as to thoroughly moisten the leaf surface and the test plants were cultivated for 8 days in the greenhouse under light. The preventive value was criticized in the same manner as in Test Example 1. The results are shown in Table 8.

TABLE 8

| Compound No. | Concentration of active ingredient (ppm) | Preventive value |
|---|---|---|
| 1 | 500 | 4 |
| 2 | 500 | 4 |
| 3 | 500 | 4 |
| 7 | 500 | 4 |
| A | 500 | 4 |
| B | 500 | 0 |

What is claimed is:

1. An adduct of the formula:

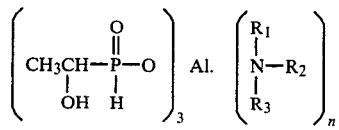

wherein $R_1$, $R_2$ and $R_3$ are each a hydrogen atom, a lower alkyl group, a lower alkoxy(lower)alkyl group, a lower alkylthio(lower)alkyl group or a cyclo(lower)alkyl group and n is a number of 0.5 to 2.0.

2. The adduct according to claim 1, wherein n is 1.0.

3. The adduct according to claim 1, wherein $R_1$, $R_2$ and $R_3$ are each a hydrogen atom, a $C_1$-$C_6$ alkyl group or a cyclo($C_3$-$C_6$) alkyl group.

4. The adduct according to claim 1, wherein $R_1$, $R_2$ and $R_3$ are each a hydrogen atom, a $C_3$-$C_6$ alkyl group or a cyclo($C_5$-$C_6$)alkyl group.

5. The adduct according to claim 1, wherein $R_1$ and $R_2$ are each a hydrogen atom and $R_3$ is a t-butyl group.

6. A process for preparing an adduct of the formula:

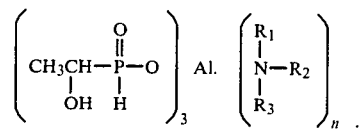

wherein $R_1$, $R_2$ and $R_3$ are each a hydrogen atom, a lower alkyl group, a lower alkoxy(lower)alkyl group, a lower alkylthio(lower)alkyl group or a cyclo(lower)alkyl group and n is a number of 0.5 to 2.0, which comprises, reacting an aluminum 1-hydroxyethylphosphinate of the formula:

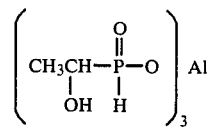

with 0.5 to 2.0 equivalents of an amine of the formula:

wherein $R_1$, $R_2$, and $R_3$ are each as defined above, in an aqueous medium at a temperature of about 0 to 60° C.

7. A composition for prevention or treatment of plant diseases caused by phytopathogenic fungi which comprises an effective amount of an adduct of the formula:

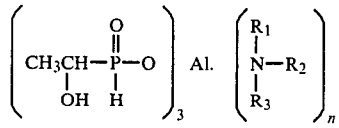

wherein $R_1$, $R_2$ and $R_3$ are each a hydrogen atom, a lower alkyl group, a lower alkoxy(lower)alkyl group, a lower alkylthio(lower)alkyl group or a cyclo(lower)alkyl group and n is a number of 0.5 to 2.0, and an inert carrier or diluent.

8. The composition according to claim 7, wherein n is 1.0.

9. The composition according to claim 7, wherein the content of the active ingredient is from 1 to 99% by weight.

* * * * *